United States Patent
Mathys et al.

(10) Patent No.: US 6,770,791 B2
(45) Date of Patent: Aug. 3, 2004

(54) PRODUCTION OF OLEFIN DIMERS AND OLIGOMERS

(75) Inventors: Georges Mathys, Bierbeek (BE); John Stephen Godsmark, Grez Doiceau (BE); Marcel Janssen, Kessel Lo (BE); Luc Roger Martens, Meise (BE); Hubertus Joseph Beckers, Keerbergen (BE); Eddy Theophile Andrea Van Driessche, Eeklo (BE); Raphael Frans Ivo Caers, Edegem (BE); John Richard Shutt, Tervuren (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/426,065

(22) Filed: Apr. 29, 2003

(65) Prior Publication Data

US 2003/0225307 A1 Dec. 4, 2003

Related U.S. Application Data

(62) Division of application No. 10/016,328, filed on Oct. 26, 2001, now abandoned
(60) Provisional application No. 60/265,700, filed on Feb. 1, 2001.

(51) Int. Cl.$^7$ .................. C07C 1/207; C07C 67/04; C07C 45/00
(52) U.S. Cl. .............. 585/327; 585/326; 585/329; 560/247; 560/244; 560/241; 568/451; 568/452

(58) Field of Search .................. 585/327, 326, 585/329; 560/247, 244, 241; 568/451, 452

(56) References Cited

U.S. PATENT DOCUMENTS

| | | | |
|---|---|---|---|
| 3,211,644 A | 10/1965 | Clark | 208/245 |
| 3,407,789 A | 10/1968 | Hallee et al. | 122/356 |
| 3,647,682 A | 3/1972 | Rabo et al. | 208/120 |
| 3,816,975 A | 6/1974 | Collins | 55/53 |
| 3,820,955 A | 6/1974 | Woebcke | 23/227 R |
| 4,499,055 A | 2/1985 | DiNicolantonio et al. | 422/197 |
| 4,814,067 A | 3/1989 | Gartside et al. | 208/127 |
| 4,828,679 A | 5/1989 | Cormier et al. | 208/120 |
| 4,861,939 A | 8/1989 | Debras et al. | 585/820 |
| 4,980,053 A | 12/1990 | Li et al. | 208/120 |
| 5,146,042 A | 9/1992 | Gurak et al. | 585/867 |
| 5,254,783 A | 10/1993 | Saleh et al. | 585/512 |
| 5,271,835 A | 12/1993 | Gorawara et al. | 208/228 |
| 5,326,465 A | 7/1994 | Yongqing et al. | 208/120 |
| 5,432,243 A | 7/1995 | Bodart | 526/68 |
| 5,434,327 A | 7/1995 | Chin et al. | 585/533 |
| 5,672,800 A | 9/1997 | Mathys et al. | 585/520 |
| 5,714,662 A | 2/1998 | Vora et al. | 585/640 |
| 6,143,942 A | 11/2000 | Verrelst et al. | 585/533 |

*Primary Examiner*—Thuan D. Dang

(57) ABSTRACT

Disclosed is an olefin containing stream from an oxygenate to olefin process, and a process for making olefin dimer and oligomer product from the olefin containing stream using a nickel based oligomerization catalyst. The dimer/oligomer product is optionally converted to hydroformylated product. The olefin containing stream that is used to make the higher olefin product has low levels of impurities including nitrogen, sulfur and/or chlorine.

22 Claims, No Drawings

PRODUCTION OF OLEFIN DIMERS AND OLIGOMERS

CROSS-REFERENCE TO RELATED APPLICATIONS

This Application is a divisional application of U.S. Ser. No. 10/016,328 filed Oct. 26, 2001 now abn. which claims the benefit of U.S. Provisional Application Serial No. 60/265,700, filed Feb. 1, 2001, which applications are both incorporated by reference herein.

FIELD OF THE INVENTION

This invention relates to an olefin stream and a method of making and using the olefin stream. In particular, the invention relates to dimerizing or oligomerizing an olefin stream using a nickel based catalyst, and optionally, hydroformylating, the dimerized or oligomerized olefin stream.

BACKGROUND OF THE INVENTION

Olefin streams containing predominantly $C_3$ to $C_5$ olefins have been used as feed for oligomerization units. Such units are particularly useful for forming dimers as well as oligomers, the terms dimer and oligomer being used interchangeably herein. The dimers and oligomers can be converted to a variety of alkanes, aldehydes, alcohols and acids.

The formation of the dimers or oligomers is conventionally accomplished by catalytic reaction. Catalysts used in the reaction are typically nickel based catalysts or acid type catalysts.

Cosyns, J. et al., in "Process for upgrading C3, C4 and C5 olefinic streams," Pet. & Coal, Vol. 37, No. 4 (1995), describe a nickel based catalyst system known as the Dimersol® process. This process is useful for dimerizing or oligomerizing a variety of olefin feeds. In particular, the process is useful for dimerizing or oligomerizing propylene, butylene and pentylene streams.

U.S. Pat. No. 6,049,017 to Vora et al., describes the dimerization of a predominantly n-butylene containing feed stream. The n-butylene feed stream is ultimately derived from an olefin stream containing a variety of butylenes produced by a methanol to olefins reaction unit. The butylene stream from the methanol to olefins unit is pretreated by a combination of partial hydrogenation of dienes and isobutylene removal by way of an MTBE process, before sending the resulting n-butylene stream to the dimerization unit.

Nickel based catalysts, such as that described by Cosyns, are particularly good for obtaining dimers having a low degree of branching. However, these catalysts are particularly sensitive to deactivation by sulfur, nitrogen, and chlorine atoms. Since these atoms are commonly present in a variety of compounds in untreated olefin feed streams, the feed streams require a substantial amount of treatment in order to remove the poisonous sulfur, nitrogen and chlorine containing compounds.

Dimers and/or oligomers which are mono-olefins, and have a low degree of branching are highly preferred. Low branching can be considered a combination of both normal olefins and mono-branched olefins, particularly monomethyl branched olefins. However, as shown in Vora, the preferred dimers and/or oligomers are conventionally obtained only after significant pretreatment of the olefin feed stream.

As the prior art references have shown, conventional methods of dimerizing and/or oligomerizing olefin feed stream to obtain desirable products have required a significant amount of pretreatment. It is desirable, therefore, to reduce the amount of required pretreatment without sacrificing the linear quality of the dimer and/or oligomer product.

SUMMARY OF THE INVENTION

This invention provides a method for obtaining a dimerized or oligomerized olefin product without using a significant amount of feed pretreatment. The product can be obtained without having to use additional means of hydrogenation or isoolefin removal, yet maintaining relatively low branching characteristics. The dimerized or oligomerized product is optionally converted to a hydroformylated product.

Specifically, the invention is directed to a method of dimerizing or oligomerizing an olefin which comprises contacting oxygenate with an olefin forming catalyst to form an olefin product. A propylene, butylene or pentylene containing stream is separated from the olefin product which contains at least 50 wt. % propylene, butylene, pentylene, or a combination thereof, and the separated olefin stream contains not greater than 1 ppm by weight sulfur calculated on an atomic basis and 0.5 to 10 wt. % isoolefin. The separated olefin stream is contacted with a nickel based oligomerization catalyst to form a dimer or oligomer product.

In another embodiment the foregoing method is followed, except the olefin forming catalyst is a silicoaluminophosphate catalyst.

In another embodiment, the separated olefin stream comprises not greater than 1 ppm by weight nitrogen. In yet another embodiment, the separated olefin stream comprises not greater than 0.5 ppm by weight chlorine. In still another embodiment the isoolefin is isobutylene.

The silicoaluminophosphate catalyst, according to one embodiment, is made from SAPO-34 or SAPO-18 molecular sieves, or a combination thereof. Preferably, the silicoaluminophosphate is an intergrowth of SAPO-34 and SAPO-18 or ALPO-18.

According to one embodiment, the dimer or oligomer product is recovered and contacted with a hydroformylating catalyst to form a hydroformylated product. According to another embodiment, the hydroformylated product is converted to an acid or alcohol. Alternatively, the acid or alcohol is converted to an ester, if desired. The ester is optionally added to a polymer composition.

The invention is also directed to an olefin composition. The composition, according to one embodiment, comprises at least 50 wt. % propylene, butylene, pentylene or a combination thereof, and contains not greater than 1 ppm by weight sulfur, not greater than 1 ppm by weight nitrogen, and not greater than 0.5 ppm by weight chlorine, each calculated on an atomic basis, and 0.5 to 10 wt. % isoolefin. The isoolefin is preferably isobutylene.

The invention further provides a method of converting an oxygenate to a hydroformylated product. The method comprises contacting oxygenate with a silicoaluminophosphate molecular sieve catalyst to form an olefin product, and separating a propylene, butylene or pentylene containing olefin stream from the olefin product, wherein the separated olefin stream comprises at least 50 wt. % propylene, butylene, pentylene, or a combination thereof, and the separated olefin stream contains not greater than 1 ppm by weight sulfur calculated on an atomic basis, and 0.5 to 10 wt. % isoolefin. The separated olefin stream is contacted with a nickel based oligomerization catalyst to form a dimer or oligomer product; and the dimer or oligomer product is contacted with a hydroformylating catalyst to form a hydroformylated product.

DETAILED DESCRIPTION OF THE INVENTION

According to this invention, desirable dimerized or oligomerized olefin product is obtained by providing an olefin feed stream that is predominantly derived from an oxygenate to olefins unit. Such a feed stream should be low in sulfur, nitrogen and chlorine content, to the extent that no or essentially no pretreatment will be required for removal of such components.

In order to obtain a product having an acceptable degree of linearity, a nickel based catalyst system is to be used. Such a system provides a highly linear dimer or oligomer product, without requiring isoolefin removal from the feed stream. If desired, olefin made from cracking a hydrocarbon stream is added to the olefin feed made from the oxygenate, according to one embodiment, as long as the total isoolefin content of the feed is not too high.

Desirably, the olefin feed stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The molecular sieve catalyst used in this invention is an oxygenate to olefin catalyst, which is defined as any molecular sieve capable of converting an oxygenate to an olefin compound. Such molecular sieves include zeolites as well as non-zeolites, and are of the large, medium or small pore type. Small pore molecular sieves are preferred in one embodiment of this invention, however. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One preferred type of olefin forming catalyst useful in this invention is one containing a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [$MeO_2$] tetrahedral unit. The [$MeO_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 microns to about 3,000 microns, more preferably from about 30 microns to about 200 microns, most preferably from about 50 microns to about 150 microns.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A preferred catalyst of this invention is a catalyst which contains a combination of SAPO-34, and SAPO-18 or ALPO-18 molecular sieve. In a particularly preferred embodiment, the molecular sieve is a crystalline intergrowth of SAPO-34, and SAPO-18 or ALPO-18.

To convert oxygenate to olefin for use as olefin feed, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

Olefins obtained by cracking hydrocarbon streams can also be used to form the olefin feed stream of this invention. It is preferable, however, that such olefins be combined with the olefin product of the oxygenate conversion reaction. This is because the olefins obtained by a cracking process are generally high in non-reactive hydrocarbon components such as alkanes, are high in branchiness, and are high in other undesirable by-products such as sulfur, which can cause conversion problems in the higher olefin reaction process. Therefore, additional purification of such a stream would be needed.

Conventional processes for removing water, oxygenates and other undesirable components from hydrocarbon streams can be used to obtain the olefin feed stream of this invention. Such methods include water washing, caustic scrubbing, distillation, and fixed bed adsorption. Other desirable methods, such as those found in *Kirk-Othmer Encyclopedia of Chemical Technology*, 4th edition, Volume 9, John Wiley & Sons, 1996, pg. 894–899, the description of which is incorporated herein by reference, can also be used. In addition, purification systems such as that found in *Kirk-Othmer Encyclopedia of Chemical Technology*, 4th edition, Volume 20, John Wiley & Sons, 1996, pg. 249–271 the description of which is also incorporated herein by reference, can be used.

The olefin feed of this invention has a substantially reduced sulfur, nitrogen and/or chlorine content. According to one embodiment, the olefin feed also contains isoolefin at a concentration that does not substantially adversely affect the linear quality of dimerized or oligomerized product. Such product contains enough n-olefin and mono-branched mono-olefin to provide derivative products, particularly esters, that are highly desirable for industrial end uses. Ester derivatives from the dimer and oligomer products of this invention will be particularly suitable for use as plasticizers.

The sulfur content of the olefin feed of this invention should be sufficiently low such that the activity of the catalyst used to form the olefin dimer or oligomer is not substantially inhibited. Preferably, the sulfur content in the olefin feed is not greater than about 1 ppm; more preferably, not greater than about 0.5 ppm; and most preferably, not greater than about 0.3 ppm by weight, calculated on an atomic basis.

The nitrogen content of the olefin feed of this invention should also be sufficiently low such that the catalytic activity of the catalyst used to form the olefin dimer or oligomer is not substantially inhibited. Preferably, the nitrogen content in the olefin feed is not greater than about 1 ppm; more preferably, not greater than about 0.5 ppm; and most preferably, not greater than about 0.3 ppm by weight, calculated on an atomic basis.

The chlorine content of the olefin feed of this invention should also be sufficiently low such that the catalytic activity of the catalyst used to form the olefin dimer or oligomer is not substantially inhibited. Preferably, the chlorine content in the olefin feed is not greater than about 0.5 ppm; more preferably, not greater than about 0.4 ppm; and most preferably, not greater than about 0.3 ppm by weight, calculated on an atomic basis.

In this invention, a nickel based oligomerization catalyst is used to provide a dimer or oligomer product. This allows for the olefin feed to contain a substantial amount of isoolefin compared to conventional processing requirements. According to this invention, the olefin feed can contain from about 0.5 to about 10 wt. % isoolefin. Preferably the olefin feed contains from about 1 to about 8 wt. % isoolefin, more preferably about 2 to about 6 wt. % isoolefin. Preferably, the isoolefin is isobutylene.

Particularly preferred in an embodiment of this invention is a mono-olefin feed stream comprising a major amount of propylene, butylene, pentylene, or a combination thereof. Preferably, the feed stream comprises at least about 50 wt. % propylene, butylene, pentylene, or a combination thereof, more preferably at least about 60 wt. % propylene, butylene, pentylene, or a combination thereof, and most preferably at least about 70 wt. % propylene, butylene, pentylene, or a combination thereof.

It is also desirable, according to one embodiment, that the olefin feed stream of this invention be high in linear mono-olefin content so as to maintain a sufficiently high conversion to higher olefin product having few branches. Preferably, the olefin feed stream comprises at least about 50 wt. % linear mono-olefin, more preferably at least about 60 wt. % linear mono-olefin; and most preferably at least about 70 wt. % linear mono-olefin. Preferably, the linear mono-olefin is a $C_2$ to $C_5$ linear mono-olefin and has a $C_6$ and higher hydrocarbon content of not greater than about 20 wt. %; more preferably, not greater than about 15 wt. %; and most preferably, not greater than about 10 wt. %.

The olefin feed streams of this invention are contacted with nickel based oligomerization catalysts in order to form desirable dimer and/or oligomer products. As used herein, dimerization and oligomerization processes are considered interchangeable terms. The processes are also known as higher olefins processes. Dimerization processes, oligomerization processes and higher olefins forming processes are all phrases that define the dimerization and/or oligomerization of light olefins, particularly $C_2$–$C_5$ olefins, to form a dimer or oligomer product, the product also referred to as a higher olefin. Examples of commercially available nickel-based catalysts used in these processes include but are not limited to Dimersol®, OCTOL® and SHOP® catalysts.

The Dimersol® process is used to oligomerize olefins with soluble nickel complexes. These complexes are described in greater detail by Yves Chauvin, Helene Olivier; in *Applied Homogeneous Catalysts with Organometallic Compounds*; edited by Boy Comils, Wolfgang A. Herrmann; Verlag Chemie, 1996, 258–268, incorporated herein by reference.

The Dimersol® process, according to one embodiment, can be carried out at a temperature ranging from about 50° C. to about 80° C. and a pressure ranging from about 1600 kPa to about 1800 kPa in a liquid phase. The catalyst is made from a catalyst precursor mixture containing a nickel salt and an aluminum based co-catalyst. The two components produce a working Ziegler nickel hydride catalyst. The catalyst components are injected separately into a reaction loop. Ammonia and water are used to neutralize the catalyst in the reaction system, and higher olefin product is separated from an aqueous phase in the reactor. The catalyst can then be recovered and recycled.

The OCTOL® process is a fixed-bed nickel catalyst system, and is used by OXENO OLEFINCHEMIE GmbH. The process is described in relative detail in *Hydrocarbon Process.*, Int. Ed. (1986) 65, 2, Sect. 1, 31–33, which is incorporated herein by reference.

Another nickel based oligomerization catalyst system is the Shell Higher Olefin Process (SHOP). The SHOP catalyst is produced in situ from a nickel salt, such as nickel chloride, sodium borohydride, and a chelating ligand. Suitable ligands are compounds of the general formula $RR^1P$-13 $CH_2$—$COR^2$. Examples of the ligand, include diphenyl phosphinoacetic acid, dicyclohexyl-phosphinoaceticd acid, and 9-(carboxymethyl)-9-phosphabicyclo[3.3.1]-nonane. The oligomerization reaction can be carried out at a temperature ranging from about 80 to about 120° C. and a pressure ranging from about 7 to about 14 MPa.

In another embodiment of a nickel-based catalyst system, oligomerization of the olefin feed stream can be carried out in the presence of a nickel oxide (NiO) catalyst such as that described in U.S. Pat. No. 5,254,783 to Saleh et al., the description of which is incorporated herein by reference. The catalyst contains amorphous NiO present as a disperse monolayer on the surface of a silica support. The catalyst desirably has a support which contains minor amounts of an oxide of aluminum, gallium or indium such that the ratio of NiO to metal oxide present in the catalyst is within the range of from about 4:1 to about 100:1.

Oligomerization using a NiO catalyst is desirably carried out in the liquid phase at temperature ranging from about 150° C. to about 275° C. A hourly weight feed rate of butene over the catalyst of from about 0.4 $hr^{-1}$ to about 1.8 $hr^{-1}$, preferably from about 0.6 $hr^{-1}$ to about 0.7 $hr^{-1}$ is preferred according to this embodiment. It is also preferred that a ratio of olefin to catalyst be from about 2:1 to about 8:1, more preferably from about 4:1 to about 6:1.

Another embodiment of a nickel based catalyst is a hydrocarbon soluble nickel carboxylate. In this embodiment, at least one inorganic compound of divalent nickel interacts with a halogenoacetic acid. The nickel inorganic compound can be a carbonate, a bicarbonate, a basic carbonate (hydroxycarbonate), a hydroxide or an oxide the halogenoacetic acid can be monochloroacetic, monofluoroacetic, dichloroacetic, tricholoracetic, difluoroacetic or trifluoroacetic. This type of catalyst is described in greater detail in U.S. Pat. No. 4,716,239, the description of which is incorporated herein by reference.

Another embodiment of a nickel based oligomerization catalyst is one that is made by mixing together a liquid mixture of at least one lithium halide with at least one hydrocarbylaluminum halide and a catalytic nickel containing mixture. The nickel mixture can be zerovalent, monovalent, or divalent complexes. This type of catalyst is described in greater detail in U.S. Pat. No. 5,723,712, the description of which is incorporated herein by reference.

Following the oligomerization reaction, the higher olefin product is optionally recovered, and further converted to desirable derivative products. These derivative products can be paraffin mixtures, obtained by conventional hydrogenation processes and optional blending and/or additional distillation. The paraffin mixtures can be used as hydrocarbon fluids and/or solvents in many applications, including paints and coatings, process fluids, metal cleaning, dry cleaning, cosmetics, pharmaceuticals, agrochemicals, degreasing, aerosol propellants, adhesives, cleaners, inks, and other industrial and household products.

Other higher olefins derivatives include thiols (often called mercaptans) or sulfides, which are produced by reacting with a sulfur compound. These are valuable starting materials for agricultural chemicals, pharmaceuticals; cosmetic ingredients, antioxidants, fragrance components and polysulfides. They are also used as polymerization regulators in rubber and plastics manufacture.

Examples of other derivatives include alkylated aromatics, using conventional alkylation processes. The alkylated aromatics can be further processed to their lubricant components or surfactant derivatives, or used as a hydrocarbon fluid as is.

A particularly desirable conversion process for higher olefins is carbonylation in general or hydroformylation in particular. These processes lead to various derivatives, including esters, aldehydes, and alcohols. An overview of catalysts and reaction conditions of hydroformylation processes is given for example by Beller et al. in *Journal of Molecular Catalysis*, A104 (1995), pages 17–85, the details of which are incorporated herein by reference. See also *Ullmanns Encyclopedia of Industrial Chemistry*, Vol. A5 (1986), pages 217 to 233; which is also incorporated herein by reference. Further description is found in J. Falbe, *Carbon Monoxide in Organic Synthesis*, 1967; and J. Falbe, *New Synthesis with Carbon Monoxide*, 1980.

Hydroformylation involves the contacting of the higher olefin product, carbon monoxide and hydrogen with the hydroformylation catalyst or its precursor. Hydroformylation catalysts are organometallic complexes of the metals of Group VIII of the periodic system, optionally used in combination as bi- or tri-metallic systems, and optionally with salts of other metals as promoters, for example tin chloride. The catalytic organometallic complexes are combinations of catalytic metals with various ligands. Preferred metals are cobalt, rhodium and palladium.

The organometallic catalyst can be introduced as the active organometallic complex, or the complexes can be made in situ from catalyst precursors and ligands introduced into a reaction zone. Suitable catalyst precursors include, for example, the respective metal hydrides, halides, nitrates, sulfates, oxides, sulfides and salts of organic acids. Such acids include formates, acetates, or heavier alkylcarboxylic acids such as oleates or naphthenates. Other organic acids which can be used include alkylsulfonic or arylsulfonic acids.

Particularly desirable complexes for the hydroformylation of the higher olefins of this invention are the carbonyl compounds of the metals mentioned, as well as those containing amines, triorganic derivatives of phosphorous, arsenic or antimony, the respective oxides of these derivatives, optionally functionalized to make them soluble in phases that under certain conditions can be separated from the organic reactor liquid.

Hydroformylation is desirably carried out at a temperature ranging from about 40° C. to about 220° C. Preferred is a temperature ranging from about 80° C. to about 200° C.; particularly about 90° C. to about 180° C.

Hydroformylation can be carried out at conventional hydroformylation pressure ranges. In general, hydroformylation is acceptable at a pressure range of from about 1 to about 400 bar gauge. Medium and high pressure ranges are preferred ranges. In general, medium and high pressure ranges are considered to be in the range of about 40 to about 400 bar gauge, more specifically in the range of about 50 to about 320 bar gauge. Within these general pressure ranges CO-liganded catalyst processes are particularly useful.

A high pressure range is generally considered in the range of about 175 to about 400 bar gauge, more desirably about 190 to about 310 bar gauge. CO-liganged rhodium and cobalt catalyst processes are particularly useful in these high pressure ranges.

A medium pressure range is generally considered to be in the range of about 40 to about 175 bar gauge, more desirably about 50 to about 150 bar gauge, and with certain catalysts it is desirable to be within a range of from about 60 to about 90 bar gauge. As an example, a triphenylphosphineoxide (TPPO)-liganded rhodium catalyst is particularly desirable in the range of from about 50 to about 150 bar guage. As another example, a trialkylphosphine-liganded cobalt catalyst is particularly desirable in the range of from about 60 to about 90 bar gauge.

Hydroformylation can also be carried out in low pressure ranges. In general, the low pressure range will be in the range of from about 5 to about 50 bar gauge, although a pressure range of from about 20 to about 30 bar gauge is particularly useful. An example of a hydroformylation catalyst which is particularly useful in the low pressure range is phosphine-liganded rhodium, more particularly triphenylphosphine-liganded rhodium.

Other hydroformylation catalysts can be used within the pressure ranges described. Such catalysts are described in *Kirk-Othmer*, 4th Edition, Volume 17, "Oxo Process," pages 902–919 and *Ullman's Encyclopedia of Industrial Chemistry*, $5^{th}$ Edition, Volume A18, "Oxo Synthesis," pages 321–327, the detailed descriptions of each being incorporated herein by reference.

It is desirable in some instances that hydroformylation be carried out at a carbon monoxide partial pressure not greater than about 50% of the total pressure. The proportions of carbon monoxide and hydrogen used in the hydroformylation or oxo reactor at the foregoing pressures are desirably maintained as follows: CO from about 1 to about 50 mol %, preferably from about 1 to about 35 mol %; and $H_2$ from about 1 to about 98 mol %, preferably from about 10 to about 90 mol %.

The hydroformylation reaction is conducted in a batch mode according to one embodiment. Alternatively, the hydroformylation reaction can occur on a continuous basis. In a continuous mode, a residence time of up to 4 hours is useful. If a plurality of reactors is employed, a residence time as short as 1 minute is advantageous. Alternatively a residence time is in the range of from about ½ to about 2 hours is useful.

Since the hydroformylation process of the invention takes place in the liquid phase and the reactants are gaseous compounds, a high contact surface area between the gas and liquid phases is desirable to avoid mass transfer limitations. A high contact surface area between the catalyst solution and the gas phase is obtainable in a variety of ways. For example and without limitation, contact surface area between the gaseous reactants and the liquid phase is obtained by stirring in a batch autoclave operation. In a continuous operation, the olefin feed stream of one embodiment is contacted with catalyst solution in, for example, a continuous-flow stirred autoclave where the feed is introduced and dispersed at the bottom of the vessel, preferably through a perforated inlet. Good contact between the catalyst and the gas feed is obtainable by dispersing a solution of the catalyst on a high surface area support. Such a technique is commonly referred to as supported liquid phase catalysis. The catalyst is provided as part of a permeable gel.

The hydroformylation reaction is performed in a single reactor according to one embodiment. Examples of suitable reactors are found in U.S. Pat. Nos. 4,287,369 and 4,287,370 (Davy/UCC); U.S. Pat. No. 4,322,564 (Mitsubishi); U.S. Pat. No. 4,479,012 and EP-A-114,611 (both BASF); EP-A-103,810 and EP-A144,745 (both Hoechst/Ruhrchemie); and U.S. Pat. No. 5,763,678 (Exxon). Two or more reactor vessels or reactor schemes configured in parallel are used in another embodiment. In addition, a plug flow reactor design, optionally with partial liquid product backmixing, provides an efficient use of reactor volume.

It is preferred, according to one embodiment, that the hydroformylation reaction be carried out in more than one reaction zone or vessel in series. Suitable reactor configurations are disclosed, for example, by Fowler et al in British Patent Specification No. 1,387,657, by Bunning et al in U.S. Pat. No. 4,593,127, by Miyazawa et al in U.S. Pat. No. 5,105,018, by Unruh et al in U.S. Pat. No. 5,367,106. and by Beckers et al. in U.S. Pat. No. 5,763,678. Examples of individual hydroformylation reactors can of the standard types described by Denbigh and Turner in Chemical Reactor Theory ISBN 0 521 07971 3, by Perry et al in *Chemical Engineers' Handbook ISBN* 0-07-085547-1 or any more recent editions, e.g., a continuous stirred tank or a plug flow reactor with adequate contact of the gas and the liquid flowing through the reactor. Advantageously these plug flow reactor designs or configurations include ways of partial backmixing of the reactor product liquid, as explained, for example, by Elliehausen et al in EP-A-3,985 and in DE 3,220,858.

Hydroformylated products have utility as intermediates in the manufacture of numerous commercially important chemicals, with the invention further providing processes in which hydroformylation is followed by reactions producing such chemicals. The reaction products will typically be a mixture of oxygenated compounds, since the higher olefin components used to make the products will generally include a mixture of components. The higher olefin components are generally a mixture of components, because the olefin feed stream that is used to make the oligomeric olefin product will generally include a mixture of olefins. However, the resulting hydroformylation product stream will generally be higher in linearity as a result of the high degree of linearity of the oligomeric olefin and olefin compositions used upstream of the hydroformylation reaction process.

Either in their pure form, or as part of the mixture in the hydroformylation product, aldehydes which are produced are optionally aldolized, a term which includes the dehydration of the aldol condensate to form an unsaturated aldehyde. This aldolization can be performed with the other aldehydes present in the stream, or with aldehydes that were prepared separately and are added to the original aldehyde or hydroformylation product stream.

Aldol product is optionally hydrogenated to the corresponding alcohol mixture. If desired, the unsaturated aldehyde mixture from aldolization can be selectively hydrogenated to the saturated aldehyde mixture. Any of the saturated aldehyde mixtures, either as made by hydroformylation or by selective hydrogenation of an aldol product, can have special value when they are oxidized to their corresponding carboxylic acids, or condensed with formaldehyde to polyols, or with ammonia to imines which can be hydrogenated to amines. The acids and polyols are valuable intermediates for esters, polyol esters, metal salts, amides, chlorides, peroxides, and again for imines and amines.

In another embodiment of the invention, the hydroformylation products of this invention are optionally hydrogenated to form saturated alcohols. Formation of a saturated alcohol may be carried out, if desired, in two stages through a saturated aldehyde, or in a single stage to the saturated alcohol, in which case it is desirable to form a saturated aldehyde as an intermediate. The alcohols are then optionally esterified, etherified, or formed into acetals or carbonates, which can be used as plasticizers, surfactants or synthetic lubricants.

The esters and ethers of the invention, or produced by the process of the invention, are suitable for use as solvents, paint coalescers, plasticizers, adhesives, surfactants, viscosity index improvers, synthetic lubricants, flame retardants, lubricant components, anti-wear agents, hydraulic fluids, cetane improvers, drilling fluids, thermoplastic and textile processing aids, polymer, especially vinyl chloride polymer, stabilizers, polymerizable monomers and fragrances.

Esterification is accomplished by reacting the alcohols of this invention with acids or anhydrides. The reaction process desirably takes advantage of conventional processes. In these conventional processes, it is desirable to react the alcohols and acids at elevated temperatures and pressures, and to drive the reaction toward completion by removing water that is produced as a by-product.

Catalysts may be employed in the esterification reaction. Suitable catalysts include, for example, titanium containing catalysts, e.g., a tetraalkyl titanate, in particular tetra-isopropyl or tetraoctyl ortho titanate, or sulphonic acid containing catalysts, e.g., p-toluene sulphonic acid or methylsulphonic acid.

Catalyst present in the esterification reaction product may be removed by alkali treatment and water washing. Advantageously, the alcohol is used in slight, e.g., from 10 to 25%, molar excess relative to the number of acid groups in the acid.

The acid of the ester may be inorganic or organic; if the latter, a carboxylic acid is preferred. Aromatic acids are preferred for plasticizer manufacture, although aliphatic acids are also employed. Additional examples of acids include, acetic, propionic, valeric, isovaleric, n-heptanoic, n-octanoic, n-decanoic, neodecanoic, lauric, stearic, isostearic, oleic, erucic, succinic, phthalic (1,2-benzenedicarboxylic), isophthalic, terephthalic, adipic, fumaric, azelaic, 2-ethylhexanoic, 3,5,5-trimethylhexanoic, 2-methylpentanoic, 2,4-dimethylheptanoic, 2,4,6-trimethylnonanoic, sebacic, trimellitic, pyromellitic, acrylic, methacrylic, tall oil, naphthenic and naphthalene-type acids, carbonic, nitric, sulphuric, phosphoric and phosphorous and their thio-analogous, acids and $C_6$ to $C_{13}$ oxo and neo acids. The esters of the $C_9$ and especially the $C_{12}$ alcohols with oxo and neo acids are especially useful as drilling fluids and power transmission fluids. Phosphate esters are particularly desirable as flame retardants; while phosphite esters provide vinyl chloride polymer stabilizers.

Esters with monobasic and dibasic acids are preferred for lubricants and lubricant components. Advantageously the resulting esters contain from 15 to 40 carbon atoms. Adipates, azelates, and phthalates are especially preferred for lubricant manufacture. Esters with unsaturated carboxylic acids, e.g., with acrylic and methacrylic acid, provide polymerizable monomers, suitable as sole or comonomer in thermoplastics manufacture, or in polymers used in or as adhesives, VI improvers, and coating resins.

The esters of the invention may be used as a plasticizer for numerous polymers. Examples include cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acids, esters of unsaturated carboxylic acids e.g., methacrylates, and/or olefins; nitrile rubbers; and post-chlorinated vinyl chloride polymers. Poly(vinyl chloride) is of particular interest.

The proportion of plasticizer ester to polymer may vary within wide limits. A desirable range is from about 10 to about 200 parts by weight per 100 parts of polymer, preferably from about 20 to about 100 parts per 100 parts of polymer.

The esters of the invention may be used alone as plasticizer, or in admixture with one another, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, or butyl benzyl phthalate, or mixtures thereof. They may also, or instead, be used with a secondary plasticizer, e.g., a chlorinated paraffin, Texanol isobutyrate, or a processing oil. If used in admixture, it is the total proportion of plasticizer that is advantageously within the ranges given above.

The plasticized polymeric compositions of the invention may be made up in numerous forms and have various end-uses. For example, they may be in the form of a dryblend, a paste, or a plastisol, depending on the grade of the resin employed. They may be used, for example, as coatings, in dipping, spraying, injection or rotational moulding, extrusion, or as self-supporting films and sheets, and may readily be foamed. End uses include flooring materials, wall coverings, moulded products, upholstery materials, leather substitutes, electrical insulation, especially wire and cable, coated fabrics, toys, and automobile parts.

The invention also provides a composition comprising an ester of the invention and a refrigerant, especially a fluorocarbon refrigerant, and more especially HFC 32 (difluoromethane) or HFC 134a (1,1,1,2-tetrafluoroethane). More especially, the invention provides such a composition also comprising at least one of a hydrolytic stability enhancer, e.g., a hindered phenol or an aromatic amine, an antioxidant, corrosion inhibitor, and a metal deactivator.

Under circumstances where the olefin feed is ultimately derived from a low-value feedstock like natural gas, i.e., in cases where methane from natural gas is converted to methanol and the methanol to olefin, the products or product mixtures may have value as liquid transportable fuels, optionally after dehydration to the olefin, and if desired hydrogenation to a paraffin or paraffinic mixture. Particularly valuable compositions produce according to this invention are isononyl alcohol mixtures, made by hydroformylation and hydrogenation of octene mixtures. The invention also provides a valuable process for the manufacture of isooctanoic acid, wherein the aldehyde from hydroformylation of a heptene mixture is separated from the hydroformylation product and subsequently oxidized.

Having now fully described this invention, it will be appreciated by those skilled in the art that the invention can be performed within a wide range of parameters within what is claimed, without departing from the spirit and scope of the invention.

What is claimed is:

1. A method of converting an oxygenate to a dimerized or oligomerized olefin product, comprising:

contacting oxygenate with a silicoaluminophosphate molecular sieve catalyst to form an olefin product;

separating a propylene, butylene or pentylene containing olefin stream from the olefin product, wherein the separated olefin stream comprises at least 50 wt. % propylene, butylene, pentylene, or a combination thereof, and the separated olefin stream contains not greater than 1 ppm by weight sulfur calculated on an atomic basis, and 25 to 10 wt. % isoolefin; and contacting the separated olefin stream with a nickel based oligomerization catalyst to form a dimer or oligomer product.

2. The method of claim 1, wherein the separated olefin stream comprises not greater than 1 ppm by weight nitrogen.

3. The method of claim 1, wherein the separated olefin stream comprises not greater than 0.5 ppm by weight chlorine.

4. The method of claim 1, wherein the separated olefin stream comprises from 1 to 8 wt. % isoolefin.

5. The method of claim 4, wherein the separated olefin stream comprises from 2 to 6 wt. % isoolefin.

6. The method of claim 1, 4 or 5, wherein the isoolefin is isobutylene.

7. The method of claim 1, wherein the silicoaluminophosphate is SAPO-34, SAPO-18, or a combination thereof.

8. The method of claim 1, wherein the silicoaluminophosphate is an intergrowth of SAPO-34 and SAPO-18 or ALPO-18.

9. The method of claim 1, further comprising recovering the dimer or oligomer product and contacting the product with a hydroformylating catalyst to form a hydroformylated product.

10. The method of claim 9, further comprising converting the hydroformylated product to an acid or alcohol.

11. The method of claim 10, further comprising converting the acid or alcohol to an ester.

12. The method of claim 11, further comprising adding the ester to a polymer composition.

13. A method of converting an oxygenate to a dimerized or oligomerized olefin product, comprising:
   contacting oxygenate with a SAPO-34 molecular sieve catalyst to form an olefin product;
   separating a propylene, butylene, or pentylene containing olefin stream from the olefin product, wherein the separated olefin stream comprises at least 50 wt. % propylene, butylene, pentylene, or a combination thereof, and the separated olefin stream contains not greater than 1 ppm by weight sulfur, not greater than 1 ppm by weight nitrogen, and not greater than 0.5 ppm by weight chlorine, each calculated on an atomic basis, and 2.5 to 10 wt. % isoolefin; and
   contacting the separated olefin stream with a nickel based oligomerization catalyst to form a dimer or oligomer product.

14. The method of claim 13, wherein the SAPO-34 catalyst further comprises SAPO-18 or ALPO-18.

15. The method of claim 13, wherein the SAPO-34 catalyst is an intergrowth of SAPO-34 and SAPO-18 ALPO-18.

16. The method of claim 13, wherein the separated olefin stream comprises from 1 to 8 wt. % isoolefin.

17. The method of claim 1, wherein the separated olefin stream comprises from 2 to 6 wt. % isoolefin.

18. The method of claim 13, 16, or 17, wherein the isoolefin is isobutylene.

19. A method of converting an oxygenate to a hydroformylated product, comprising:
   contacting oxygenate with a silicoaluminophosphate molecular sieve catalyst to form an olefin product;
   separating a propylene, butylene or pentylene containing olefin stream from the olefin product, wherein the separated olefin stream comprises at least 50 wt. % propylene, butylene, pentylene, or a combination thereof, and the separated olefin stream contains not greater than 1 ppm by weight sulfur calculated on an atomic basis, and 2.5 to 10 wt. % isoolefin;
   contacting the separated olefin stream with a nickel based oligomerization catalyst to form a dimer or oligomer product; and
   contacting the dimer or oligomer product with a hydroformylating catalyst to form a hydroformylated product.

20. The method of claim 19, further comprising converting the hydroformylated product to an acid or alcohol.

21. The method of claim 20, further comprising converting the acid or alcohol to an ester.

22. The method of claim 21, further comprising adding the ester to a polymer composition.

* * * * *

UNITED STATES PATENT AND TRADEMARK OFFICE
CERTIFICATE OF CORRECTION

PATENT NO. : 6,770,791 B2
DATED : August 3, 2004
INVENTOR(S) : Georges Mathys et al.

It is certified that error appears in the above-identified patent and that said Letters Patent is hereby corrected as shown below:

Column 14,
Line 67, the number "25", should read -- 2 --.

Column 15,
Line 10, the number "1", should read -- 2 --.

Column 16,
Line 2, the number "2.5", should read -- 2 --.
Line 12, the number "1", should read -- 2 --.
Line 26, the number "2.5", should read -- 2 --.

Signed and Sealed this

Eighth Day of March, 2005

JON W. DUDAS
*Director of the United States Patent and Trademark Office*